United States Patent [19]

Ridgway, Jr. et al.

[11] 4,258,070
[45] Mar. 24, 1981

[54] METHOD FOR INHIBITING MICROBIAL GROWTH IN FOOD PROCESSES

[75] Inventors: John A. Ridgway, Jr., La Porte, Ind.; William P. Weisrock, Naperville, Ill.

[73] Assignee: Standard Oil Company (Indiana), Chicago, Ill.

[21] Appl. No.: 948,331

[22] Filed: Oct. 4, 1978

Related U.S. Application Data

[63] Continuation-in-part of Ser. No. 810,293, Jun. 27, 1977, abandoned.

[51] Int. Cl.$^3$ .................. C12C 11/24; C12B 1/24; C12N 1/16; C12N 1/04
[52] U.S. Cl. .................. 426/495; 426/60; 426/520; 426/521; 435/255; 435/260; 435/800
[58] Field of Search .................. 426/60, 62, 520, 521, 426/522, 495; 435/800, 940, 255, 944, 242, 260

[56] References Cited

U.S. PATENT DOCUMENTS

| | | | |
|---|---|---|---|
| 1,801,095 | 4/1931 | Levin | 435/242 |
| 2,072,748 | 3/1937 | Fuchs | 426/60 X |
| 2,705,215 | 3/1955 | Griesbach | 435/255 X |

OTHER PUBLICATIONS

White, J., Yeast Technology, John Wiley and Sons, Inc., N.Y., 1954, (pp. 66–70) TP460W5C,2.
Rosen, K., Manufacture of Bakers' Yeast, Process Biochemistry, 1968 (pp. 45–47), TP500P68.

Primary Examiner—David M. Naff
Attorney, Agent, or Firm—Gregory E. Croft; William T. McClain; William H. Magidson

[57] ABSTRACT

A method for inhibiting microbial contamination, particularly applicable to processes for preparing food materials under nominally aseptic conditions, is carried out by cycling the temperature of a desired portion of the process which is a source of contamination between upper and lower limits which fall between 0° and 60° C. and which are at least 5° C. apart at a frequency of about 0.2 to 5 cycles per hour to create a varying thermal environment at the source of contamination which slows microbial growth.

14 Claims, No Drawings

METHOD FOR INHIBITING MICROBIAL GROWTH IN FOOD PROCESSES

This application is a continuation-in-part of copending application Ser No. 810,293, now abandoned.

BACKGROUND OF THE INVENTION

1. Field of the Invention

This invention relates to methods for reducing microbial growth in processes for the preparation or production of heat sensitive materials. More particularly, it relates to the inhibition of microbial contamination in processes for the production of food materials. Most particularly, it relates to the nominally aseptic production of single-cell protein materials such as yeasts.

2. Description of the Prior Art

Processes for the preparation of heat sensitive materials such as foods and food ingredients are generally required to meet stringent standards for cleanliness. Oftentimes there is a particular portion or segment of the process which is most vulnerable to bacterial contamination and which must be continually cleaned to maintain the product within specifications. Such cleaning operations are often time-consuming and expensive.

For example, during the processing of torula yeasts produced by continuous fermentation, a continuous centrifugation step is employed to concentrate the yeast broth from the fermentor (approximately 4 wt. percent solids) to a yeast cream (approximately 15 wt. percent solids). The centrifuge and ancillary piping, pumps, etc. are most susceptible to contamination by microorganisms which can build up in the system. Because high temperatures will damage the yeast cell, process temperatures much above 50° C., such as those employed for pasteurization, cannot be employed at this stage of the process. Therefore, contamination in this portion of the process necessitates the use of daily clean-up procedures as a preventative measure, which generally involves using alternate centrifuges such that one is in service while the other is being cleaned. It would be extremely desirable to avoid this cumbersome procedure altogether or at least reduce the rate of contamination and hence the frequency at which cleaning must be performed.

Accordingly, it is an object of this invention to provide a method for reducing the rate of growth in microorganisms which may proliferate as contaminants in such systems. This and other objects will become apparent from further reading of this specification.

SUMMARY OF THE INVENTION

In one aspect of the invention resides in an improved process for producing a microbiologically acceptable heat sensitive material, the improvement comprising cycling the temperature of any selected portion of the process which is a source of microbial contamination between upper and lower limits falling in the range of from 0° to 60° C. which are at least 5° C. apart and at a frequency of from about 0.2 to about 5 cycles per hour to inhibit microbial growth. The source of microbial contamination can be any piping, apparatus, or portion thereof which provides either an opening through which contaminants can enter the system or a place within the system where microbial contaminants can collect and multiply, such as dead spots, corners, crevices, or simply solid surfaces where build-up of product can occur. The temperature limits depend largely upon the type of food material being processed and the residence time of the food material at the selected temperatures. If high temperatures are selected, it is generally necessary that the residence time be very short in order to prevent degradation or leaching of the food product. It is important here to distinguish the difference between the residence time of the food material in the selected portion of the process being subjected to the temperature cyclization, as opposed to the cycle time of the temperature cycle. Referring again to torula yeast production, for example, it has been found that the centrifuge used to concentrate the yeast cream is a source of contamination to the process system. Cycling the temperature of the centrifuge during processing has been found to be effective in maintaining sanitary conditions for longer periods of time. It has been found that yeast cell suspensions can be held at about 50° C. for the short period of time required to pass through the centrifuge without a significant amount of leakage of cellular material from the yeast cells (yield loss of about 0.35 wt. percent). The time spent by each yeast cell in passing through the centrifuge is its residence time and is dependent upon the flow rate of the stream. On the other hand, the cycle time for the temperature cycle at the centrifuge is independent of the flow rate and can be adjusted to be as long or as short as is necessary to achieve the desired thermal environment at that particular portion of the overall process. Any contaminating microorganisms which would otherwise thrive in the centrifuge must contend with varying temperature in order to multiply. It has been found that temperature cycling for a portion of a process retards the growth of such contaminating microorganisms in that portion of the process. For purposes herein, "portion of the process" refers to any apparatus and/or the space within such apparatus which is used to carry out the process in question. It particularly includes all vessels, piping, pumps, separation equipment, etc.

In another aspect, the invention resides in an improved process for producing single-cell food material, the improvement comprising inhibiting microbial contamination of the food material by cycling the temperature of a portion of the process which is a source of contamination between upper and lower limits falling between about 30° C. and 50° C. which are at least 5° C. apart and at a frequency of from about 0.2 to about 5 cycles per hour.

More specifically, the invention resides in the above-said method wherein the single-cell food material is a yeast and wherein the temperature is cycled between about 30° and 50° C. at a frequency of about 0.5 to 2 cycles per hour, preferably about one cycle per hour.

Still more specifically, the invention resides in an improved process for producing yeast wherein a yeast suspension stream, such as a fermentor effluent, is concentrated by centrifugation, the improvement comprising repetitively cycling the temperature of said stream between about 30° and 50° C. at a frequency of from about 0.2 to about 5 cycles per hour, preferably about 0.5 or 1 cycle per hour.

Those skilled in the art will appreciate that the precise temperature limits within the range of 0° C. to 60° C. will be determined by the particular food material being processed and by the extent to which higher temperatures affect the product quality. In general, the difference between the upper limit temperature and the lower limit temperature should be as extreme as is possible and at least 5° C., taking into consideration the economics of achieving temperature control and the effects of temperature on the product yield. Temperature cycles of less than 5° C. will have little effect upon bacterial contaminants. The temperature cycling of any portion of a process can be accomplished in any suitable manner such as direct temperature control or by cycling the temperature of the material being transferred before it passes through the portion of the process in question, thereby functioning as a heat transfer medium. This invention can be advantageously applied to any process for sanitation control of pathogenic bacterial contaminants.

DESCRIPTION OF THE PREFERRED EMBODIMENT

A pilot plant test was designed to determine whether temperature cycling between 30° C. and 50° C. would discourage microbial growth in a continuously operated centrifuge used to concentrate fermentor effluent from the continuous fermentation of a torula yeast, *Candida utilis*. The lower cycle temperature of 30° C. was chosen because it is the normal process temperature for the fermentor effluent. Temperatures down to 0° C. could also have been used, however. The upper cycle temperature of 50° C. was chosen because it had a minimal effect on the product yield (0.35 wt. percent yield loss) and when used as the upper limit of the temperature cycle was effective in preventing growth of most bacteria, yeasts, and molds, particularly pathogenic microorganisms. An upper cycle temperature of up to 60° C. could also have been used and would have been very effective for controlling contamination, but such a temperature would have too much of a deleterious effect on the product yield to be economical in this particular process. The fermentor effluent contains about 3 wt % yeast solids, typically free from microbial contamination, and is concentrated by centrifugation to a solids content of about 12-15 wt % in the centrifuge effluent. Because it is difficult to keep the centrifuge free of bacteria, microbial contamination rapidly builds up in the centrifuge and its effluent in the 24 hour interval between CIP (clean-in-place) cleanings.

In this test the temperature of the fermentor effluent was alternately raised to 50° C. in a Kontro Thermalizer (wiped film heat exchanger) and allowed to return to ambient (30° C.) in a two-hour cycle, i.e. one hour at 50° C. and one hour at 30° C. The effluent material passed directly to the centrifuge and thence to the spray drier. The effluent material therefore acted as a heat transfer medium and correspondingly cycled the temperature of the centrifuge. Samples were taken hourly during the day and at 3-hour intervals overnight at sample points located before and after the heat exchanger and after the centrifuge.

Conditions at the start of the test were as follows: the fermentor effluent was contaminated at a low level (less than 100/ml. expressed as bacteria/ml.) and remained so for the duration of the test. Contamination in the effluent from the Kontro heat exchanger was also low (less than 200/ml.) and remained thus. The contamination at the outlet of the centrifuge was high (approximately $2 \times 10^5$/ml.) due to growth of bacteria in the centrifuge.

The data on contamination in the centrifuge effluent over the period of the test are shown in TABLE I. It is readily apparent that during the first two cycles of temperature which were initiated at $T=0$ hours, the contamination steadily decreased, such that by the third cycle the count was 10/ml., or a 4 log reduction in bacteria.

TABLE I

| Centrifuge Effluent Contamination During the Test Period | | | | | | | | | | | | | |
|---|---|---|---|---|---|---|---|---|---|---|---|---|---|
| Time (hours) | −1 | 0 | 2 | 3 | 4 | 5 | 6 | 7 | 8 | 9 | 13 | 16 | |
| Bacteria/ml. | $8 \times 10^4$ | $2 \times 10^5$ | 500 | 1900 | 120 | 10 | 10 | 10 | 10 | 20 | 20 | 10 | |
| Time (hours) | 19 | 22 | 23 | 24 | 25 | 26 | 27 | 28 | 29 | 30 | 31 | 32 | 33 |
| Bacteria/ml. | 30 | 30 | 90 | 60 | 420 | 1300 | 240 | 125 | 130 | 450 | 260 | 600 | 200 |
| Time (hours) | 37 | 40 | 43 | 46 | 47 | 48 | 53 | | | | | | |
| Bacteria/ml. | 2200 | $2 \times 10^4$ | 2500 | $1.5 \times 10^4$ | 6000 | $10^5$ | $3 \times 10^4$ | | | | | | |

Contamination remained below 100 bacteria per ml. for 24 hours and generally below 1000 per ml. for an additional 8 hours, at which time the bacterial level started to increase once again.

The data in TABLE II show, by contrast, the normal buildup of contamination in the centrifuge effluent after CIP cleaning.

TABLE II

| | Centrifuge Effluent Contamination During Normal Operations | | | | | | | |
|---|---|---|---|---|---|---|---|---|
| Time (hours) | 0 | 3 | 9 | 17 | 25 | 45 | 52 | 60 |
| Total Bacteria/ml. | 20 | 70 | 1860 | $1.2 \times 10^6$ | $5.6 \times 10^6$ | $2 \times 10^7$ | $1.5 \times 10^7$ | $1.4 \times 10^7$ |
| Coliforms/ml. | 10 | 40 | 10 | 510 | $3.7 \times 10^3$ | $5.3 \times 10^3$ | $1.5 \times 10^4$ | $2 \times 10^5$ |

Normally bacterial counts of $10^6$/ml. are seen before $T=20$ hours, along with significant coliform-type contaminants.

Referring again to TABLE I, bacterial levels in the centrifuge effluent increased between $T=33$ hours and $T=44$ hours, in spite of continued temperature cycling. When cycling was stopped at $T=45$ hours and the temperature maintained at 30° C., contamination attained a level of about $10^5$/ml. No coliform bacteria were noted until after the temperature cycling was discontinued.

The bacterial contaminants which persisted in growing during the latter stages of temperature cycling were isolated and characterized as to temperature requirements. We found that these bacteria were facultative thermophiles, that is, capable of growth at either cycling temperature. These were not apparent at the start of the experiment. Thus the data in TABLES I and II show that cycling of temperatures within a moderate range of 30° C. to 50° C. extended the time required to reach a contamination level of 2000 per ml. from 9 hours to about 36 hours, and at the same time reducing coliform contamination to undetectable levels for 45 hours instead of 16-20 hours. This would permit CIP cleaning once every 48 hours rather than once every 24 hours, thus reducing downtime, increasing productivity, and reducing CIP chemicals cost.

Based on these results we infer that a decrease in the cycling time to one hour or less would prolong the suppression of contamination, particularly for pathogenic bacteria, for more than 20 hours, possibly indefinitely. This inference is based on the fact that the 30 minutes interval between temperature changes is approaching the minimum generation time for most bacteria. Therefore the probability would be high that a temperature change would occur during the division cycle of any particular bacterium, thus interfering with its growth and replication.

As previously stated, the proper temperatures and cycle times will vary with the type of food material being produced. The specific embodiment shown here for purposes of illustration should not be construed as limiting, and it will be apparent to those skilled in the art that many variations from this example can be made without departing from the scope of this invention.

We claim:

1. A method for inhibiting microbial contamination occurring in a process for producing heat sensitive materials, said method comprising cycling the temperature of any portion of the process which is a source of contamination between upper and lower limits falling in the range between 0° and 60° C. and at a frequency of from about 0.2 to about 5 cycles per hour, said upper and lower limits being at least 5° C. apart.

2. The process of claim 1 wherein the lower and upper temperature limits fall in the range between about 30 and about 50° C., respectively.

3. The process of claim 1 wherein the temperature is cycled between about 30° and 50° C. at a frequency from about 0.5 to 2 cycles per hour.

4. The process of claim 1 wherein the heat sensitive material is a food material.

5. The process of claim 4 wherein the food material is a yeast.

6. The process of claim 1 wherein the temperature at the source of contamination is cycled by cycling the temperature of the material passing therethrough.

7. The process of claim 1 wherein the temperature at the source of contamination is cycled by direct temperature control.

8. The process of claim 1 wherein the source of contamination is a centrifuge.

9. The process of claim 1 wherein the temperature is cycled at a frequency of about one cycle per hour.

10. In a process for producing yeast wherein a yeast suspension stream is concentrated by centrifugation, the improvement comprising inhibiting microbial contamination contributed by the centrifuge by repetitively cycling the temperature of said stream between upper and lower temperature limits falling in the range between about 50° C. and about 30° C. at a frequency of from about 0.2 to about 5 cycles per hour, said upper and lower temperature limits being at least 5° C. apart.

11. The process of claim 10 wherein the upper and lower temperature limits are about 50° C. and about 30° C. respectively.

12. The process of claim 11 wherein the temperature is cycled at a frequency of about 0.5 cycles per hour.

13. The process of claim 11 wherein the temperature is cycled at a frequency of about 2 cycles per hour.

14. The process of claim 13 wherein the yeast is *Candida utilis*.

* * * * *